(12) United States Patent
Saikou

(10) Patent No.: US 12,161,287 B2
(45) Date of Patent: Dec. 10, 2024

(54) SURGERY ASSISTANCE APPARATUS, SURGERY ASSISTANCE METHOD, AND COMPUTER-READABLE RECORDING MEDIUM

(71) Applicant: NEC Corporation, Tokyo (JP)

(72) Inventor: Masahiro Saikou, Tokyo (JP)

(73) Assignee: NEC CORPORATION, Tokyo (JP)

(*) Notice: Subject to any disclaimer, the term of this patent is extended or adjusted under 35 U.S.C. 154(b) by 676 days.

(21) Appl. No.: 17/430,030

(22) PCT Filed: Feb. 7, 2020

(86) PCT No.: PCT/JP2020/004948
§ 371 (c)(1),
(2) Date: Aug. 11, 2021

(87) PCT Pub. No.: WO2020/166528
PCT Pub. Date: Aug. 20, 2020

(65) Prior Publication Data
US 2022/0133129 A1    May 5, 2022

(30) Foreign Application Priority Data
Feb. 13, 2019  (JP) .................................. 2019-024022

(51) Int. Cl.
*G06V 10/22*   (2022.01)
*A61B 1/00*    (2006.01)
(Continued)

(52) U.S. Cl.
CPC .. *A61B 1/000094* (2022.02); *A61B 1/000095* (2022.02); *A61B 1/0005* (2013.01);
(Continued)

(58) Field of Classification Search
CPC ........ A61B 1/000094; A61B 1/000095; A61B 1/0005; A61B 1/00055; A61B 1/00045;
(Continued)

(56) References Cited

U.S. PATENT DOCUMENTS

2012/0092472 A1    4/2012  Higuchi
2012/0274754 A1    11/2012 Tsuruoka
(Continued)

FOREIGN PATENT DOCUMENTS

JP    2011-160848 A    8/2011
JP    2012-085696 A    5/2012
(Continued)

OTHER PUBLICATIONS

English translation of Written opinion for PCT Application No. PCT/JP2020/004948, mailed on Apr. 21, 2020.
(Continued)

*Primary Examiner* — Charlotte M Baker
(74) *Attorney, Agent, or Firm* — Sughrue Mion, PLLC

(57) ABSTRACT

A surgery assistance apparatus 1 that improves the accuracy of surgery by presenting stable assistance information (display/sound) to a surgeon includes a calculation unit 2 that calculates, based on a living-body internal image 21 captured using an endoscope 42, region information indicating the region of a target part image 22 corresponding to a target part and probability information indicating a probability of the target part image 22 being an image of the target part, and a generation unit 3 that generates assistance information for assisting surgery while suppressing an extreme change when one of or both a change in the region information and a change in the probability information are extreme.

9 Claims, 12 Drawing Sheets

(51) Int. Cl.
*G06F 18/22* (2023.01)
*G06T 7/00* (2017.01)

(52) U.S. Cl.
CPC .......... *A61B 1/00055* (2013.01); *G06F 18/22* (2023.01); *G06T 7/0014* (2013.01); *G06V 10/22* (2022.01); *G06T 2207/10068* (2013.01); *G06T 2207/30004* (2013.01); *G06V 2201/03* (2022.01)

(58) Field of Classification Search
CPC .................. G06F 18/22; G06T 7/0014; G06T 2207/10068; G06T 2207/30004; G06V 10/22; G06V 2201/03; G06V 10/761; G06V 10/25
USPC ......................................................... 382/128
See application file for complete search history.

(56) References Cited

U.S. PATENT DOCUMENTS

| | | |
|---|---|---|
| 2015/0077529 A1 | 3/2015 | Hatta et al. |
| 2016/0148053 A1 | 5/2016 | Matsuzaki |
| 2018/0242817 A1 | 8/2018 | Imaizumi et al. |
| 2020/0129042 A1 | 4/2020 | Takahashi et al. |
| 2020/0170485 A1 | 6/2020 | Takahashi et al. |
| 2020/0297422 A1* | 9/2020 | Gocho .................. A61B 34/25 |

FOREIGN PATENT DOCUMENTS

| | | |
|---|---|---|
| JP | 2013-258627 A | 12/2013 |
| JP | 2015-032127 A | 2/2015 |
| JP | 6315873 | 4/2018 |
| JP | 6315873 B2 | 4/2018 |
| WO | 2018/216617 A1 | 11/2018 |
| WO | 2018/216618 A1 | 11/2018 |

OTHER PUBLICATIONS

International Search Report for PCT Application No. PCT/JP2020/004948, mailed on Apr. 21, 2020.

* cited by examiner

Fig.7
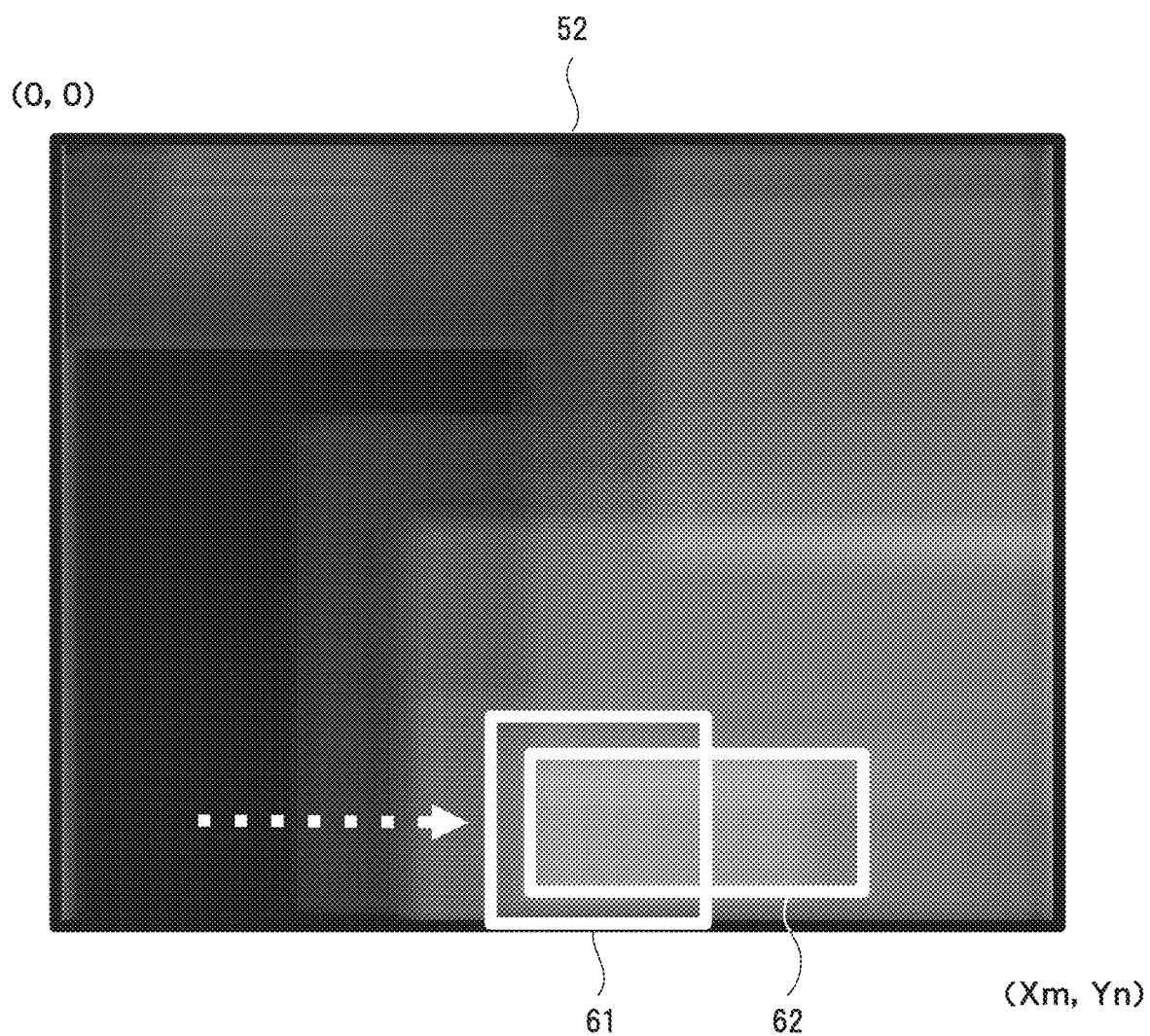
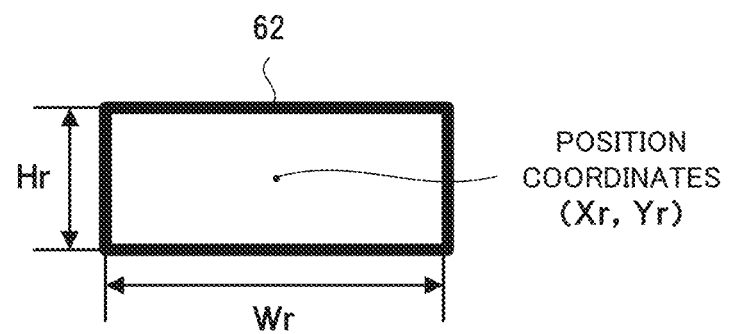

Fig.8

| | | |
|---|---|---|
| LIVING-BODY INTERNAL IMAGE | 51 | |
| FEATURE AMOUNT f | f = (f1, f2, ⋯ fn) | |
| FEATURE AMOUNT r | r1 = (X1, Y1, W1, H1, conf1) | |
| | r2 = (X2, Y2, W2, H2, conf2) | |
| | r3 = (X3, Y3, W3, H3, conf3) | |
| | r4 = (X4, Y4, W4, H4, conf4) | |

81

SURGERY ASSISTANCE APPARATUS, SURGERY ASSISTANCE METHOD, AND COMPUTER-READABLE RECORDING MEDIUM

This application is a National Stage Entry of PCT/JP2020/004948 filed on Feb. 7, 2020, which claims priority from Japanese Patent Application 2019-024022 filed on Feb. 13, 2019, the contents of all of which are incorporated herein by reference, in their entirety.

TECHNICAL FIELD

The present invention relates to a surgery assistance apparatus and a surgery assistance method for assisting endoscopic surgery, and further relates to a computer readable recording medium that includes a program for realizing the surgery assistance apparatus and the surgery assistance method recorded thereon.

BACKGROUND ART

A surgery assistance apparatus that assists a surgeon performing surgery by notifying the surgeon that a target human-body-part image has been extracted from an endoscopic image is known. In an example of a notification technique, when a human-body-part image corresponding to a tumor that is likely to become cancerous is extracted from an endoscopic image, the human-body-part image is highlighted or a sound is produced to notify the surgeon that a target human-body-part image has been extracted.

Here, "highlight" refers to display in which graphics, a color, or the like that make it easy for the surgeon to recognize the region of a human-body-part image is used, display indicating information regarding a human-body-part image, and the like. In addition, methods for producing a sound includes methods for notifying the surgeon via the surgeon's acoustic sense based on sound pitch, sound volume, and audio guidance.

As described above, with the above-described surgery assistance apparatus, as a result of notifying a surgeon that a target human-body-part image has been extracted, it is possible to keep the surgeon from overlooking the human-body-part image. Therefore, the accuracy of the surgery can be improved.

In addition, as a related technique, Patent Document 1 discloses an endoscope image processing apparatus for presenting, to a surgeon, a report display indicating that a human-body-part image has been extracted and a probability display indicating the probability of false detection of the human-body-part image.

LIST OF RELATED ART DOCUMENTS

Patent Document

Patent Document 1: Japanese Patent No. 6315873

SUMMARY

Technical Problems

However, in the technique disclosed in Patent Document 1 and the like, the image capture state of a captured image of a human body part changes for each frame influenced by the operation of an endoscope and the like. Due to this, informing display to a surgeon also undergoes extreme changes. Specifically, informing display for assisting a surgeon undergoes extreme changes, and inhibits surgery. This makes it difficult for the surgeon to view the human-body-part image, for example. Therefore, the accuracy of the surgery decreases.

Examples of an "extreme change" include a change such as flickering of graphics used for highlighting and color blinking when blur, camera shake, and the like that occur due to operation of an endoscope, the influence of the surrounding environment, and the like frequently arise. A case is also included in which, when a sound is produced, the sound pitch, the sound volume, and the audio guidance frequently changes, which is unpleasant to the ear.

An example object of the invention is to provide a surgery assistance apparatus, a surgery assistance method, and a computer readable recording medium that improve the accuracy of surgery by presenting stable assistance information (display/sound) to a surgeon.

Solution to the Problems

In order to achieve the above-described example object, a surgery assistance apparatus according to an example aspect of the invention includes:

a calculation unit configured to calculate, based on a living-body internal image captured using an endoscope, region information indicating a region of a target part image corresponding to a target part and probability information indicating a probability of the target part image being an image of the target part; and a generation unit configured to generate assistance information for assisting surgery while suppressing an extreme change when one of or both a change in the region information and a change in the probability information are extreme.

In addition, in order to achieve the above-described example object, a surgery assistance method according to an example aspect of the invention includes:

calculating, based on a living-body internal image captured using an endoscope, region information indicating a region of a target part image corresponding to a target part and probability information indicating a probability of the target part image being an image of the target part; and generating assistance information for assisting surgery while suppressing an extreme change when one of or both a change in the region information and a change in the probability information are extreme.

Furthermore, in order to achieve the above-described example object, a computer-readable recording medium according to an example aspect of the invention includes a program recorded thereon, the program including instructions that cause a computer to carry out:

calculating, based on a living-body internal image captured using an endoscope, region information indicating a region of a target part image corresponding to a target part and probability information indicating a probability of the target part image being an image of the target part; and generating assistance information for assisting surgery while suppressing an extreme change when one of or both a change in the region information and a change in the probability information are extreme.

Advantageous Effects of the Invention

As described above, according to the invention, the accuracy of surgery can be improved by presenting stable assistance information (display/sound) to a surgeon.

BRIEF DESCRIPTION OF THE DRAWINGS

FIG. 7 is a diagram for illustrating calculation of a feature amount r.

FIG. 8 is a diagram for illustrating an example of the data structure of feature amount information.

EXAMPLE EMBODIMENT

Example Embodiment

Figure 1:
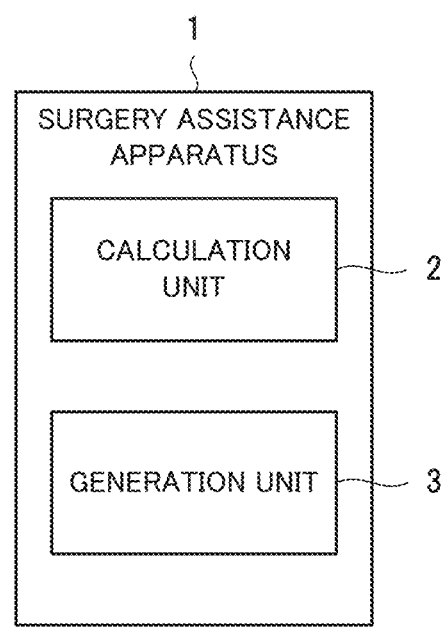
FIG. 1 is a diagram for illustrating an example of a surgery assistance apparatus.

An example embodiment of the invention will be described below with reference to FIGS. 1 to 12.
[Apparatus Configuration]
First, the configuration of a surgery assistance apparatus 1 according to the present example embodiment will be described with reference to FIG. 1. FIG. 1 is a diagram for illustrating an example of the surgery assistance apparatus 1.

The surgery assistance apparatus shown in FIG. 1 is an apparatus for improving the accuracy of surgery by presenting stable display to a surgeon. In addition, as shown in FIG. 1, the surgery assistance apparatus 1 includes a calculation unit 2 and a generation unit 3.

Of these units, the calculation unit 2 calculates, based on a living-body internal image captured using an endoscope, region information indicating the region of a target part image corresponding to a target part and probability information indicating a probability of the target part image being an image of the target part. The generation unit 3 generates assistance information for assisting surgery while suppressing an extreme change when one of or both a change in the region information and a change in the probability information are extreme.

Note that the assistance information includes one or more of highlighting information that is used for highlighting a region, probability display information that is used for probability display, and sound information for making a notification, with sound, that a target part image has been extracted.

Thus, according to the example embodiment, assistance information (one or more of highlighting information, probability display information, and sound information) is generated according to one of or both a change in the region of a target part image and a change in the probability. Therefore, even when the image capture state of a captured target part image changes for each frame influenced by operation of an endoscope and the like, and the image capture state of the target part image undergoes an extreme change, it is possible to suppress an extreme change in the assistance information. Accordingly, it is possible to prevent the target part image from being difficult for the surgeon to see while preventing assistance information from inhibiting surgery. Therefore, the accuracy of the surgery can be improved.

Figure 2:
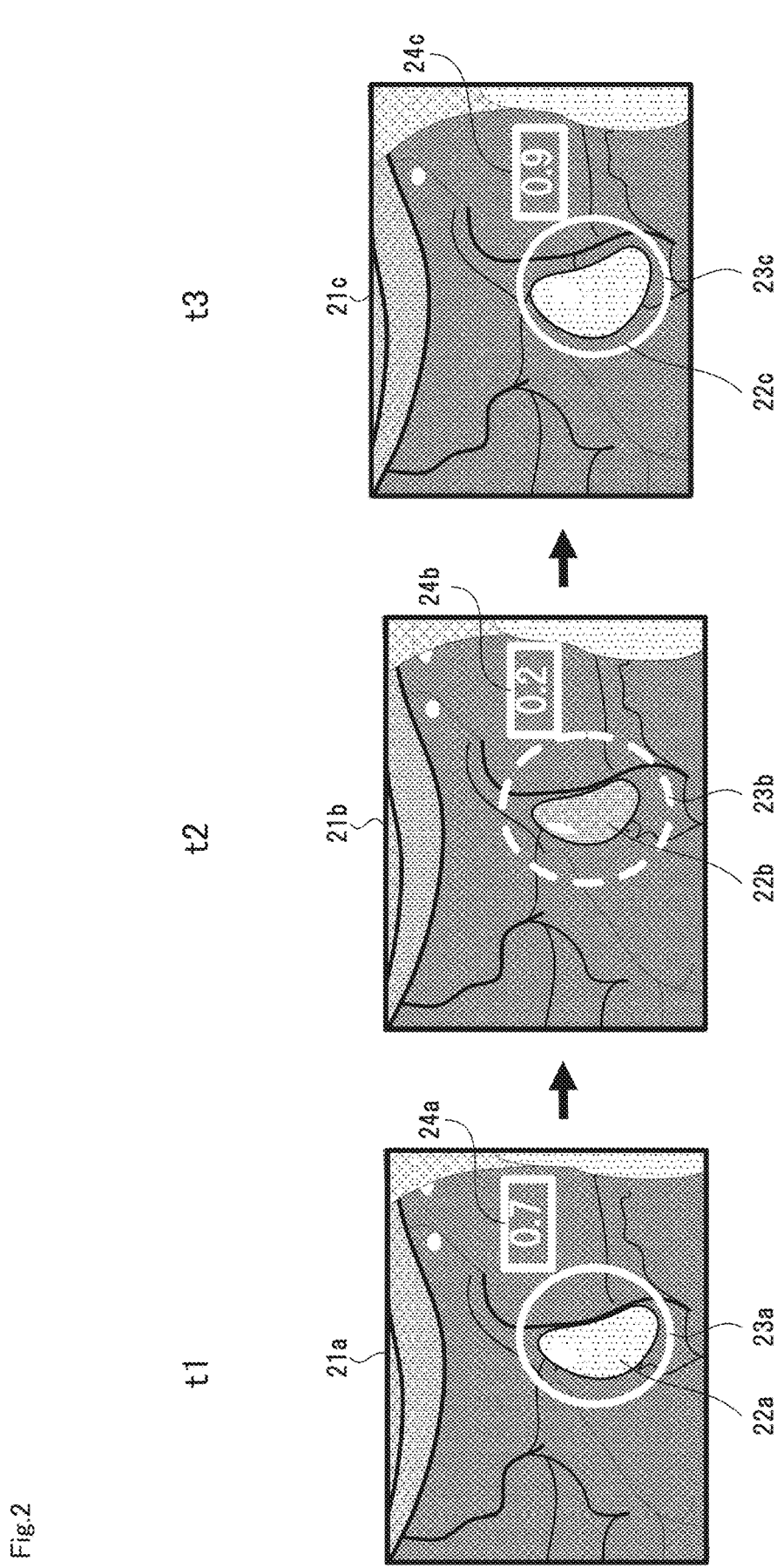
FIG. 2 is a diagram for illustrating an example of conventional highlighting and probability display.
Figure 3:
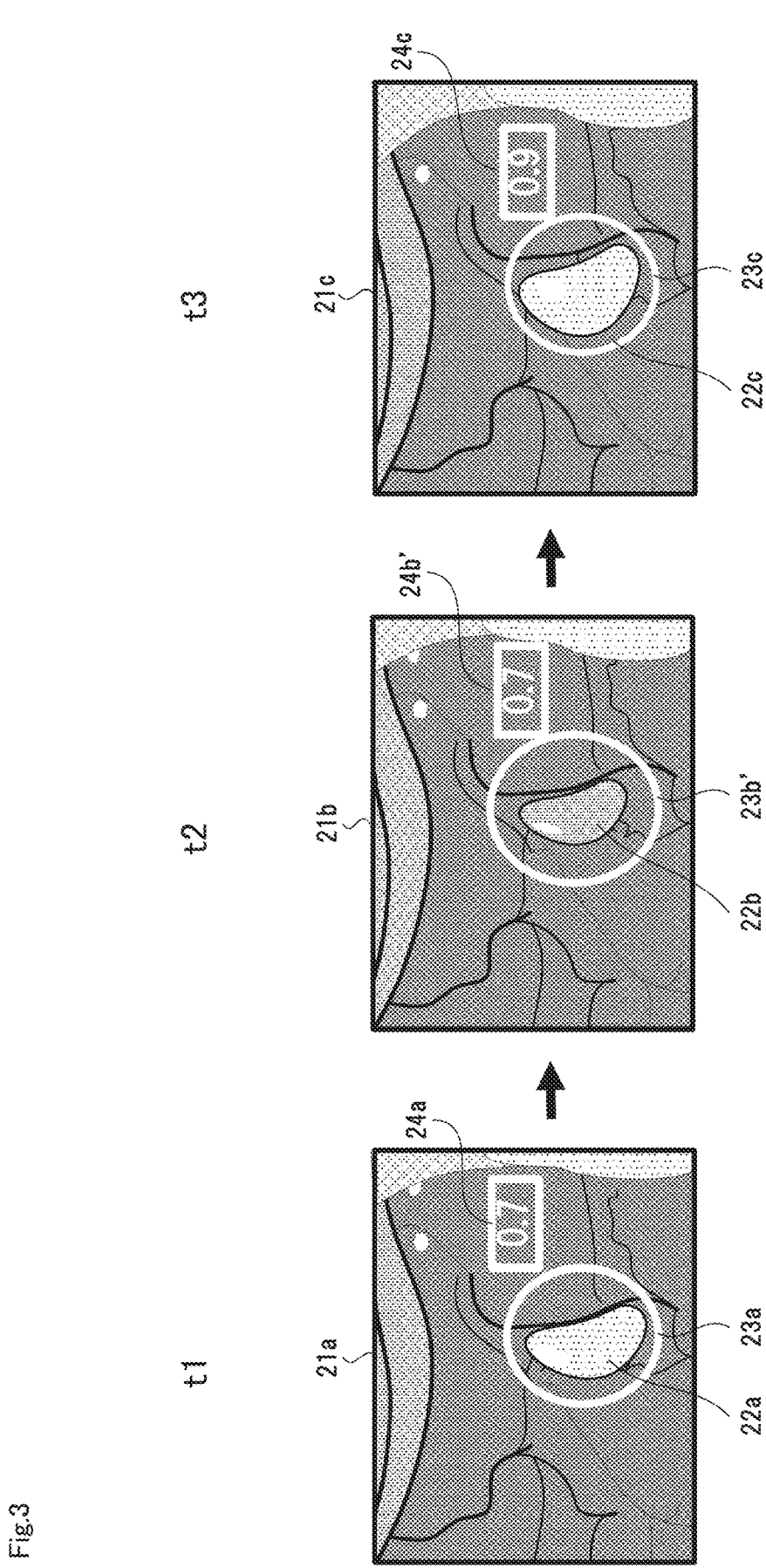
FIG. 3 is a diagram for illustrating an example of highlighting and probability display according to an example embodiment of the present invention.

A detailed description will be given with reference to FIGS. 2 and 3. FIG. 2 is a diagram for illustrating an example of conventional highlighting and probability display. FIG. 3 is a diagram for illustrating an example of highlighting and probability display according to the example embodiment. Note that target part images 22 in FIGS. 2 and 3 are images corresponding to a tumor, for example.

In addition, the surgeon is notified that a target part image 22 has been extracted, utilizing sound pitch, sound volume, audio guidance, and the like as sound information.

In the example in FIG. 2, the probability of a target part image 22a at time t1 is 0.7, which is higher than or equal to a preset threshold of 0.6, and thus an ellipse with a solid white line is displayed as highlighting 23a. Next, at time t2, the probability of a target part image 22b is 0.2, which is lower than the threshold of 0.6, and thus an ellipse with a white broken line is displayed as highlighting 23b. Next, at time t3, the probability of a target part image 22c is 0.9, which is higher than or equal to the threshold of 0.6, and thus an ellipse with a solid white line is displayed as highlighting 23c. Note that the threshold is a value that is used for switching highlighting.

However, when an extreme change in the probability such as that described above continues, the ellipse with a solid white line and the ellipse with a white broken line are alternately displayed, and thus highlighting for assisting a surgeon actually hinders the surgery conducted by the surgeon.

In addition, in the example in FIG. 2, probability display 24 that differs for each of the images 21a to 21c is displayed, and thus the probability display 24 is not displayed in a fixed manner. Therefore, the probability display hinders the surgery conducted by the surgeon. Furthermore, when the colors of the highlighting and probability display are changed in accordance with a change in the probability, such a change further hinders the surgery conducted by the surgeon.

In addition, in the example in FIG. 2, the probability display 24 that differs for each of the images 21a to 21c is displayed, that is, the target part image 22 is detected and not detected depending on the image, and thus a sound is not output in a fixed manner. Therefore, sound hinders the surgery conducted by the surgeon. Furthermore, when the sound pitch, the sound volume, the audio guidance, and the like in addition to the colors of the highlighting and probability display are changed in accordance with a change in the probability, such a change further hinders the surgery conducted by the surgeon.

In view of this, according to the example embodiment, highlighting and probability display such as that shown in FIG. 3 are performed. In the example in FIG. 3, even if the probability of the target part image 22b at time t2 in FIG. 2 is 0.2, the highlighting 23b is not displayed as an ellipse with a white broken line, and instead an ellipse with a solid white line is displayed as indicated by highlighting 23b'. Accordingly, even if the probability rapidly changes (undergoes an extreme change), the highlighting 23 is displayed as the same ellipse with a solid white line (displayed without flickering) from time t1 to t3, and as a result, the surgery conducted by the surgeon is not hindered.

In addition, in the example in FIG. 3, even if the probability of the target part image 22b at time t2 in FIG. 2 is 0.2, probability display 24b of 0.2 is not displayed, and 0.7 or 0.9 is displayed as probability display 24b' that is the same as probability display 24a at time t1 or probability display 24c at t3. With such a configuration, probability display is made unlikely to undergo an extreme change (prevented from flickering). Therefore, probability display is performed such that the surgery conducted by the surgeon is not hindered, and thus the accuracy of the surgery can be improved. Note that the average of the probability at time t1 and the probability at time t3, which is 0.8, may be used as the probability display 24 at time t2.

In addition, in the example in FIG. 3, even if the probability of the target part image 22b at time t2 in FIG. 2 is 0.2, sound information is not changed to the sound pitch and the sound volume corresponding to 0.2, and the same sound as the probability display 24a at time t1 or the probability display 24c at t3 is output. With such a configuration, also regarding sound information, sound is made unlikely to extremely change (prevented from being unpleasant to the ear). Therefore, a sound is output such that the surgery conducted by the surgeon is not hindered, and thus the accuracy of the surgery can be improved.

[System Configuration]

Figure 4:
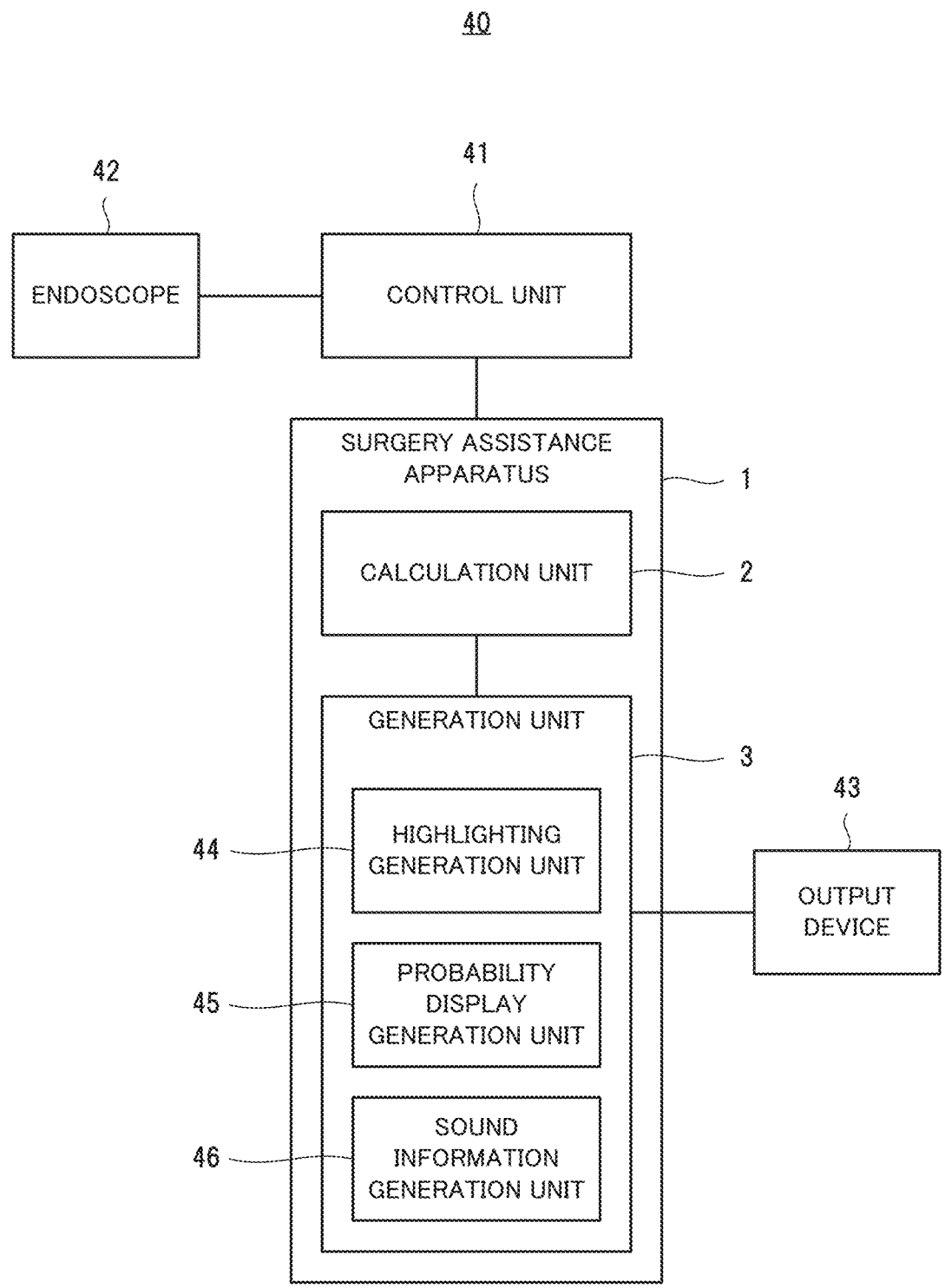
FIG. 4 is a diagram for illustrating an example of a system that includes the surgery assistance apparatus.

Next, the configuration of the surgery assistance apparatus 1 according to the example embodiment will be described in more detail with reference to FIG. 4. FIG. 4 is a diagram for illustrating an example of a system that includes the surgery assistance apparatus.

As shown in FIG. 4, a system 40 according to the example embodiment includes a control unit 41, an endoscope 42, and an output device 43 in addition to the surgery assistance apparatus 1. In addition, the generation unit 3 includes a highlighting generation unit 44, a probability display generation unit 45, and a sound information generation unit 46.

The control unit 41 is a video processor or the like that executes image processing and the like on an input image. Specifically, the control unit 41 obtains captured image signals from the endoscope 42, performs image adjustment and the like on the captured image signals, generates living-body internal images 21, and outputs the generated living-body internal images 21 to the surgery assistance apparatus 1.

The endoscope 42 transmits each living-body internal image 21 obtained by capturing an image of the inside of a living body such as a human body, to the control unit 41 connected to the endoscope 42. The endoscope 42 includes, for example, an insertion unit that is inserted into a living body, an image-capturing unit that is provided on the leading end side of the insertion unit, an operation unit for controlling bending of the insertion unit, image capturing by the image-capturing unit, etc., and a connection unit that connects the endoscope 42 and the surgery assistance apparatus 1. In addition to the image-capturing unit, the endoscope 42 also includes an illumination unit, a nozzle used for feeding air and water and for suction, a forceps port, and the like on the leading end side of the insertion unit.

The output device 43 obtains, from the generation unit 3, output information (to be described later) converted into a format that can be output, and outputs images, sound, etc., generated based on the output information. Note that the output device 43, for example, includes an image display device that uses liquid crystals, organic electroluminescence (EL), or a cathode ray tube (CRT), and further includes a sound output device such as a speaker, and the like. Note that the output device 43 may also be a printing device such as a printer.

The surgery assistance apparatus will be described in detail.

The calculation unit 2 calculates, for each of a plurality of living-body internal images 21 captured in time series using the endoscope 42, region information indicating the target part image 22 corresponding to a target part and probability information indicating a probability of the target part image 22 being an image of the target part.

Specifically, first, the calculation unit 2 obtains a living-body internal image 21 from the endoscope 42 via the control unit 41. Next, the calculation unit 2 extracts feature amounts f from the living-body internal image 21.

LBP (Local Binary Pattern) is used as an example of a method for extracting the feature amounts f from the living-body internal image 21. The LBP is described in a document "T. Ojala, M. Pietikainen, and D. Harwood, "Performance evaluation of texture measures with classification based onkullback discrimination of distributions," inProc. IEEE Int. Conf. Patt. Recogn., 1994", for example. Note that the method for extracting the feature amounts f is not limited to a method that uses LBP, and any method that can extract the feature amounts f from the living-body internal image 21 may be used.

Figure 5:
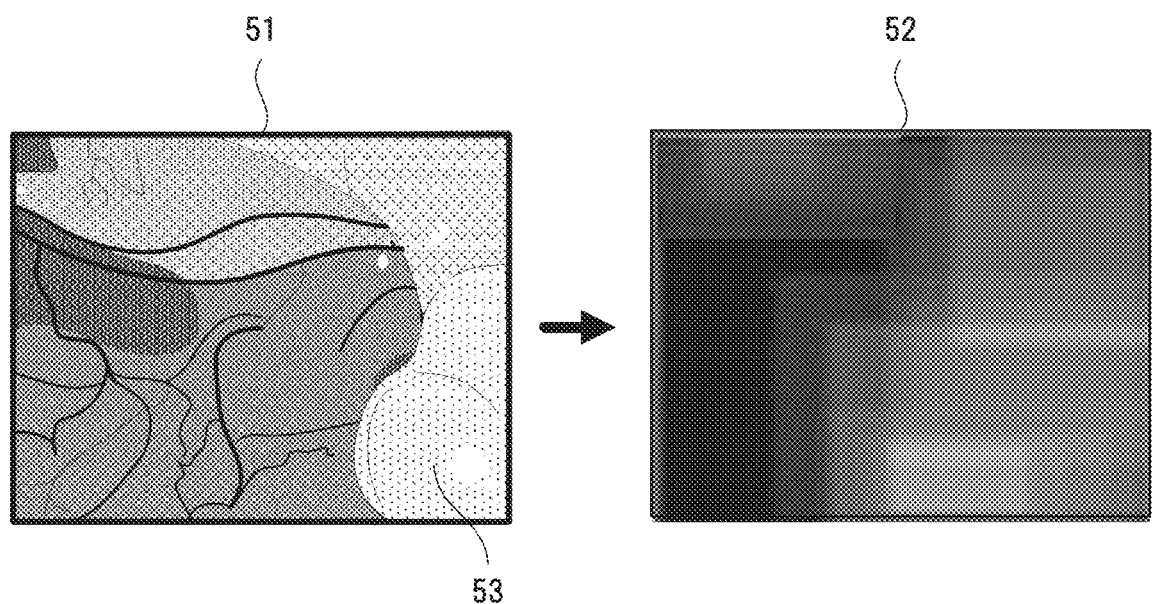
FIG. 5 is a diagram for illustrating an example of a living-body internal image and an image showing feature amounts f.

FIG. 5 is a diagram for illustrating an example of a living-body internal image and an image indicating feature amounts f. A living-body internal image 51 shown in FIG. 5 is obtained by capturing an image of the inside of a large intestine, and a target part image 53 is obtained by capturing an image of a tumor. FIG. 5 also shows an image 52 indicating feature amounts f extracted from each living-body internal image 51. Note that, in the image 52 in FIG. 5, features of the target part are indicated by regions that are white or a similar color, and the rest is indicated by black regions.

Next, the calculation unit 2 applies processing for detecting the target part image 22 such as sliding window, to an image corresponding to the feature amounts f generated from the living-body internal image 21, and calculates a feature amount r for each living-body internal image 21. The feature amount r is calculated using features in windows 61 and 61', for example.

Figure 6:
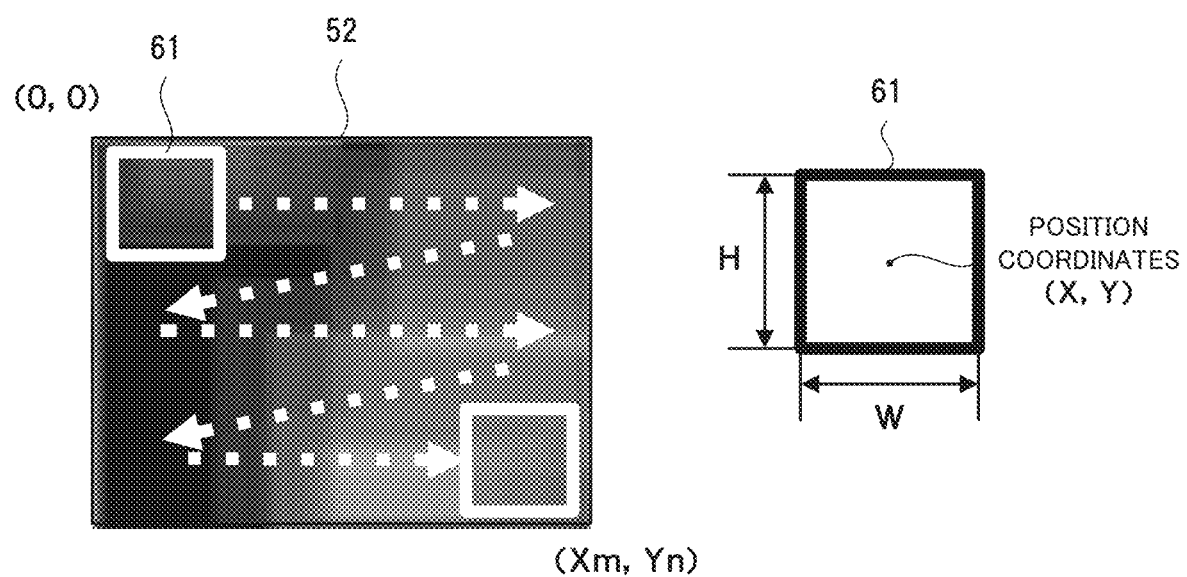
FIG. 6 is a diagram for illustrating calculation of a feature amount r.

FIGS. 6 and 7 are diagrams for illustrating the calculation of the feature amount r. With respect to the image 52 corresponding to the feature amounts f, for example, the calculation unit 2 shifts the window 61 (window region) in the directions of the white arrows shown in FIG. 6 (in a predetermined order), and calculates a feature amount each time the window 61 is shifted (each time the window 61 is moved by a predetermined distance). In addition, the calculation unit 2 changes the size of the window 61, uses the window 61' thereby having a different size, and shifts the window 61' in a predetermined order, and calculates a feature amount each time the window 61' is shifted. Note that the predetermined order is not limited to that in the directions of the white arrows (horizontal direction) shown in FIG. 6.

The windows 61 and 61' will be described. If the image 52 is regarded as a two-dimensional coordinate system, position information indicating the positions of the windows 61 and 61' is indicated by some coordinates in the window 61. The center coordinates (X, Y) shown in FIG. 6 are one example of such coordinates in the window 61. If the image 52 is regarded as a two-dimensional coordinate system, size information indicating the size of the window 61 is indicated by the width (W) and height (H) of the window 61 as shown in FIG. 6.

The feature amount r will be described. As represented by a region 62 shown in FIG. 7, region information of the feature amount r is indicated by the center coordinates (Xr, Yr) of a rectangle circumscribing the target part and size information indicating the size of the rectangle (the width (Wr) and height (Hr) of the rectangle).

Note that the center coordinates of the rectangle circumscribing the target part may be indicated by a relative position to the window 61, i.e., (Xr'=Xr−X, Yr'=Yr−Y). The probability information is information indicating a probability (conf) of the region of a detection target part corresponding to the target part, the probability being calculated using the features in the window 61.

Note that the feature amount r may be expressed as: feature vector r=(Xr', Yr', Wr, Hr, conf). Furthermore, the region information of the feature amount r need not have a rectangular shape. The shape may be circular, elliptical, or the like.

Note that the calculation unit 2 stores, in a storage device (not illustrated), each living-body internal image 51 and the above-described feature amounts f and r in association with each other. FIG. 8 is a diagram for illustrating an example of the data structure of feature amount information. In FIG. 8, in feature amount information 81 that indicates the feature amounts f and r, the feature amount f corresponding to the living-body internal image and the feature amount r (r1, r2, r3, r4) are associated with each other. Note that the storage device may be provided inside or outside of the control unit 41.

The generation unit 3 generates output information that is used by the output device 43 to output an image. The output information is information that is used for the output device 43 to output living-body internal images 21, target part images 22, highlighting 23, probability display 24, sound information, and the like.

The generation unit 3 will be described in detail.

The highlighting generation unit 44 calculates the number of probabilities that are higher than or equal to a threshold and the number of probabilities that are lower than the threshold using probabilities of a plurality of living-body internal images 21 captured before and after a target living-body internal image 21, and generates highlighting information in accordance with the calculated numbers of probabilities. Specifically, the highlighting generation unit 44 makes a majority decision using the number of probabilities that are higher than or equal to the threshold and the number of probabilities that are lower than the threshold, and generates highlighting information in accordance with the result of the majority decision.

A case will be described in which each frame before and after a target frame is used.

When a majority decision is made using each living-body internal image 21 captured before and after the target living-body internal image 21, if both the probabilities of the living-body internal images 21 captured before and after the target living-body internal image 21 are higher than or equal to the threshold, even if the probability of the target living-body internal image 21 is lower than the threshold, the highlighting generation unit 44 generates highlighting information that is used to display the same highlighting 23 as the living-body internal images 21 captured before and after the target living-body internal image 21.

Figure 9:
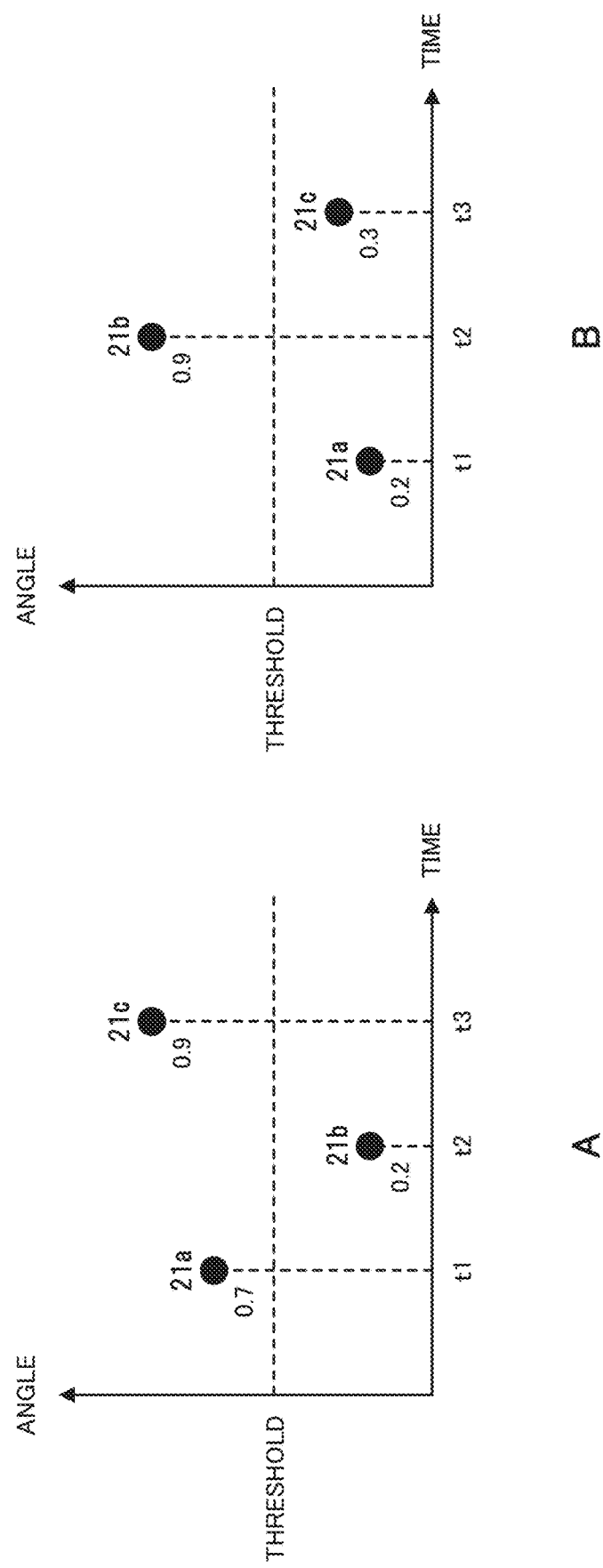
FIG. 9 is a diagram for illustrating generation of highlighting information.

FIG. 9 is a diagram for illustrating generation of highlighting information. FIG. 9A is a diagram for illustrating the relationship between living-body internal images 21a to 21c shown in FIG. 2 and probabilities corresponding thereto. The probability (=0.7) of the target part image in the living-body internal image 21a, the probability (=0.2) of the target part image in the living-body internal image 21b, and the probability (=0.9) of the target part image in the living-body internal image 21c are shown. In such a case, as shown in FIG. 3, the highlighting generation unit 44 generates highlighting information that is used to display an ellipse with a solid white line as highlighting, which is the same highlighting 23 as that of the living-body internal images 21a and 21c.

Conversely, if both the probabilities of the living-body internal images 21 captured before and after the target living-body internal image are lower than the threshold, even if the probability of the target living-body internal image 21 is higher than or equal to the threshold, the highlighting generation unit 44 generates highlighting information that is used to display the same highlighting 23 as the living-body internal images 21 captured before and after the target living-body internal image 21.

As shown in FIG. 9B, for example, when the probabilities of the target part images in the living-body internal images 21a to 21c are respectively 0.2, 0.9, and 0.3, and highlighting 23a and highlighting 23c before and after the highlighting 23b are expressed as an ellipse with a white broken line, the highlighting generation unit 44 generates highlighting information that is used for displaying, as the highlighting 23b, the same ellipse with a solid white line as the highlighting 23a and the highlighting 23c.

A case will be described in which several frames before and after a target frame are used.

When a majority decision is made using a plurality of living-body internal images 21 captured before and after the target living-body internal image 21, the highlighting generation unit 44 determines whether or not the probability of each of the living-body internal images 21 captured before and after the target living-body internal image 21 is higher than or equal to the threshold, and calculates the number of living-body internal images 21 for which the probability is higher than or equal to the threshold, and the number of living-body internal images 21 for which the probability is lower than the threshold.

If the number of living-body internal images 21 for which the probability is higher than or equal to the threshold is the larger, the highlighting generation unit 44 generates highlighting information for displaying the highlighting 23 that is used when the probability is higher than or equal to the threshold. The highlighting generation unit 44 displays the highlighting 23, for example, using the above-described ellipse with a solid white line.

On the other hand, if the number of living-body internal images 21 for which the probability is lower than the threshold is the larger, the highlighting generation unit 44 generates highlighting information for displaying the highlighting 23 that is used when the probability is lower than the threshold. The highlighting generation unit 44 displays the highlighting 23, for example, using the above-described ellipse with a white broken line.

A case will be described in which a similarity is taken into consideration.

Figure 10:
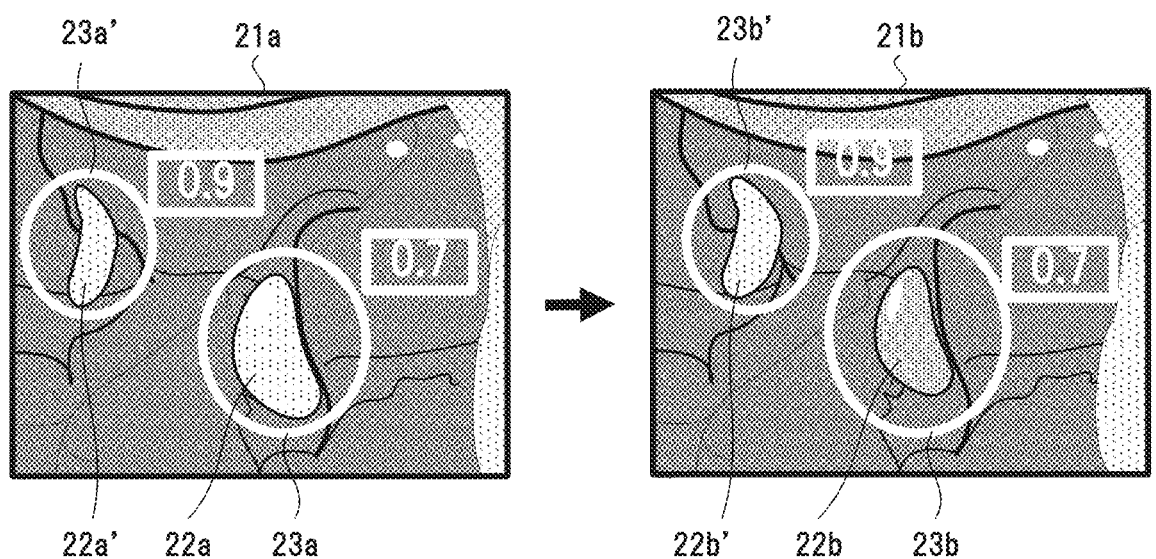
FIG. 10 is a diagram for illustrating generation of highlighting information.

FIG. 10 is a diagram for illustrating generation of highlighting information. As shown in FIG. 10, when there are two target part images 22a and 22a' in the living-body internal image 21a, and there are the two target part images 22b and 22b' in the living-body internal image 21b, the target part image 22 cannot be identified, for example, and it is conceivable that the highlighting 23a corresponding to the target part image 22a will be displayed in the target part image 22b', and not in the target part image 22b. In view of this, the highlighting 23 is displayed in consideration of the similarity between target part images 22.

The highlighting generation unit 44 calculates the similarity between a region corresponding to the target part image 22 of the target living-body internal image 21 and each of the regions corresponding to the target part images 22 of the plurality of living-body internal images 21 captured before and after the target living-body internal image 21.

Specifically, the highlighting generation unit 44 calculates the similarity in the feature amounts f and r between different living-body internal images 21. In calculation of the similarity between living-body internal images 21, the distance between the feature vector of the feature amount f and the feature vector of the feature amount r is calculated. Alternatively, the similarity may also be expressed using a linear sum.

The highlighting generation unit 44 then generates highlighting information in accordance with the number of probabilities that are higher than or equal to the threshold and the number of probabilities that are lower than the threshold, for each region for which the calculated similarity is higher than or equal to a similarity threshold. The similarity threshold is a value that is used for determining whether or not different target part images are similar, for example.

A case will be described in which a similarity and the positions of regions are used.

Specifically, the highlighting generation unit 44 obtains the center coordinates of region information as the position of a region corresponding to the target part image 22 of the target living-body internal image 21. The highlighting generation unit 44 also obtains the center coordinates of region information as the position of each of the regions corresponding to the target part images 22 of a plurality of living-body internal images 21 captured before and after the target living-body internal image 21.

Next, the highlighting generation unit 44 calculates the shift amount between the center coordinates of the region corresponding to the target part image 22 of the target living-body internal image 21 and the center coordinates of each of the regions corresponding to the target part images 22 of the plurality of living-body internal images 21 captured before and after the target living-body internal image 21. The highlighting generation unit 44 then selects living-body internal images 21 corresponding to shift amounts that are lower than or equal to a position threshold, from among the calculated shift amounts. The position threshold is a value that is used for determining whether or not different target part images are shifted from each other, for example.

Next, the highlighting generation unit 44 calculates the number of probabilities that are higher than or equal to the threshold and the number of probabilities that are lower than the threshold, using the selected living-body internal images 21. The highlighting generation unit 44 then makes a majority decision using the number of probabilities that are higher than or equal to the threshold and the number of probabilities that are lower than the threshold, and generates highlighting information corresponding to the target part image 22 of the target living-body internal image 21 in accordance with the result of the majority decision, as described above.

Thus, as a result of taking the similarity into consideration, even if there are a plurality of target part images, the same target part image 22 can be accurately highlighted. Accordingly, a different target part image is not highlighted, and thus it is possible to prevent highlighting from hindering the surgery conducted by the surgeon. Therefore, the accuracy of the surgery is improved.

The probability display generation unit 45 extracts the image capture state of a living-body internal image 21, and generates probability display information in accordance with the extracted image capture state. The image capture state is one of or a combination of two or more of the state of blur of the target part image, the state of camera shake, the state of color distribution, the state of coloration, and the state of contrast.

The image capture state is described in a document "Yan Ke, Xiaoou Tang, Feng Jing, "The Design of High-Level Features for Photo Quality Assessment" School of Computer Science, Carnegie Mellon; Microsoft Research Asia CVPR2006. https://www.cs.cmu.edu/~yke/photoqual/cvpr06photo.pdf", for example. Note that a method for extracting an image capture state is not limited to the above method, and any method that can extract an image capture state from a living-body internal image may be used.

Specifically, the probability display generation unit 45 obtains probability information from the calculation unit 2, corrects the obtained probability information C using Expression 1, and generates a probability $C_i'$.

$$C_i' = w_{i,0}C_i + w_{i,1}S_1 + w_{i,2}S_2 + \ldots + w_{i,n}S_n \qquad \text{[Expression 1]}$$

$S_i$: score for blur, camera shake, color distribution, coloration, and contrast $W_{i,x}$: weighting coefficient for each score In addition, the probability $C_i'$ of m living-body internal images 21 captured before the target living-body internal image 21 may also be corrected based on Expression 2 and be used.

$$C_i'' = \sum_m \gamma^{i-m} C_i' \qquad \text{[Expression 2]}$$

$\gamma^{v-m} < 1$: forgetting coefficient

Thus, since it is possible to suppress an extreme change of a probability by correcting the probability, there is no extreme change in the probability display 24, making it possible to ensure that the surgery conducted by the surgeon is not hindered. Therefore, the accuracy of the surgery is improved.

The sound information generation unit 46 extracts the image capture state of a living-body internal image 21, and generates sound information in accordance with the extracted image capture state. Specifically, the sound information generation unit 46 obtains the corrected probability from the probability display generation unit 45, and causes the output device 43 to output a sound based on a sound pitch and a sound volume corresponding to the corrected probability.

The sound information generation unit 46 uses the obtained probability to reference information in which the probability and sound information (information that includes at least one of the sound pitch, the sound volume, and the audio guidance) corresponding to the probability are associated with each other, for example, and generates sound information that is to be output to the output device 43.

[Apparatus Operations]

Figure 11:
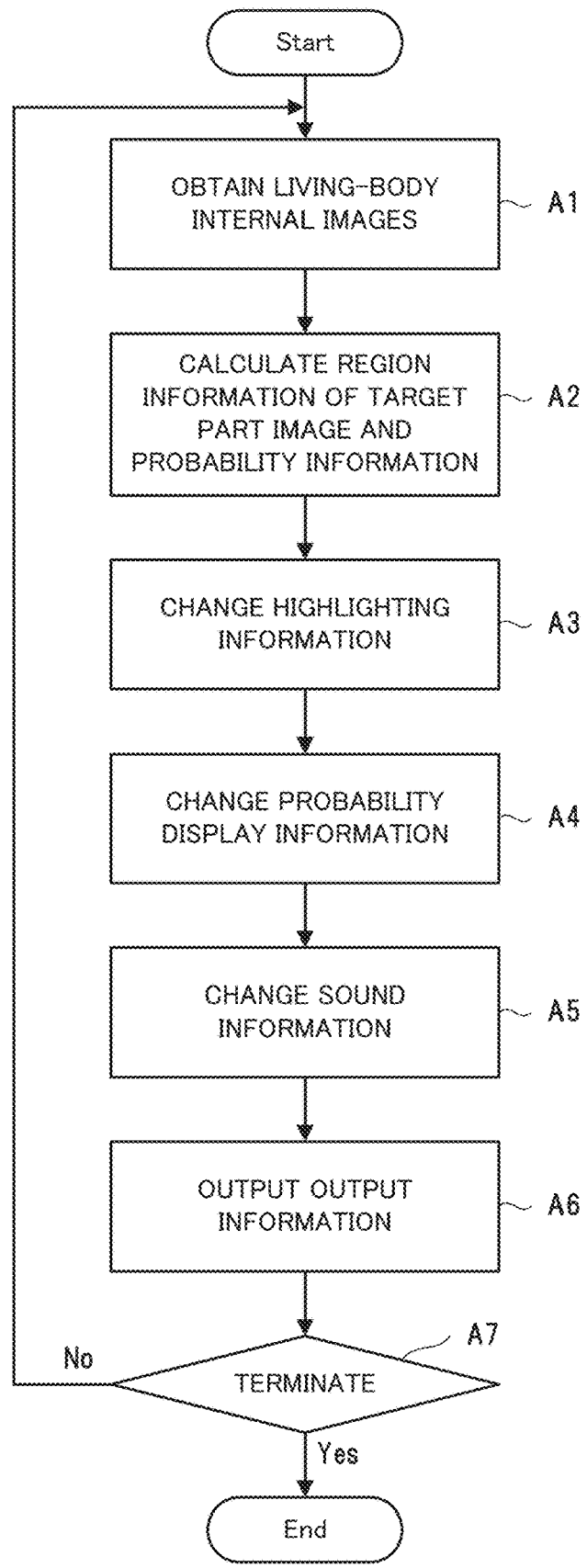
FIG. 11 is a diagram for illustrating an example of operations of the surgery assistance apparatus.

Next, the operations of the surgery assistance apparatus in the example embodiment of the invention will be described with reference to FIG. 11. FIG. 11 is a diagram for illustrating an example of the operations of the surgery assistance apparatus. FIGS. 2 to 10 will be referred to as needed in the following description. Furthermore, in the example embodiment, a surgery assistance method is carried out by causing the surgery assistance apparatus 1 to operate. Accordingly, the following description of the operations of the surgery assistance apparatus is substituted for the description of the surgery assistance method in the example embodiment.

As shown in FIG. 11, first, the control unit 41 obtains captured image signals from the endoscope 42, performs image adjustment on the captured image signals, generates living-body internal images 21, and outputs the generated living-body internal images 21 to the surgery assistance apparatus 1 (step A1).

Next, the calculation unit 2 calculates, based on the living-body internal images 21, region information indicating a target part image 22 corresponding to a target part and probability information indicating the probability of the target part image being an image of the target part (step A2). Specifically, in step A2, the calculation unit 2 first extracts, from each of the living-body internal images 21, the feature amounts f corresponding to the target part image. Next, in step A2, the calculation unit 2 applies processing for detecting the target part image 22 such as sliding window, to an image corresponding to the feature amounts f generated from the living-body internal image 21, and calculates the feature amount r for each of the living-body internal images 21.

Next, the generation unit 3 generates output information that is used to cause the output device 43 to output images, and outputs the generated output information to the output device 43 (steps A3 and A4). The output information is information that is used for the output device 43 to output living-body internal images 21, target part images 22, highlighting 23, probability display 24, and the like.

Specifically, the highlighting generation unit 44 calculates the number of probabilities that are higher than or equal to the threshold and the number of probabilities that are lower than the threshold, using the probabilities of a plurality of living-body internal images 21 captured before and after the target living-body internal image 21, and generates highlighting information in accordance with the calculated numbers of probabilities (step A3). Specifically, in step A3, the highlighting generation unit 44 makes a majority decision using the number of probabilities that are higher than or equal to the threshold and the number of probabilities that are lower than the threshold, and generates highlighting information in accordance with the result of the majority decision.

A case will be described in which each frame before and after a target frame is used.

In step A3, when a majority decision is made using each living-body internal image 21 captured before and after the target living-body internal image 21, if both the probabilities of the living-body internal images 21 captured before and after the target living-body internal image 21 are higher than or equal to the threshold, even if the probability of the target living-body internal image 21 is lower than the threshold, the highlighting generation unit 44 generates highlighting information that is used for displaying the same highlighting 23 as the living-body internal images 21 captured before and after the target living-body internal image 21.

Conversely, in step A3, if both the probabilities of the living-body internal images 21 captured before and after the target living-body internal image are lower than the threshold, even if the probability of the target living-body internal image 21 is higher than or equal to the threshold, the highlighting generation unit 44 generates highlighting information that is used for displaying the same highlighting 23 as the living-body internal images 21 captured before and after the target living-body internal image 21.

A case will be described in which several frames before and after a target frame are used.

In step A3, when a majority decision is made using a plurality of living-body internal images 21 captured before and after the target living-body internal image 21, the highlighting generation unit 44 determines whether or not the probability of each of the living-body internal images 21 captured before and after the target living-body internal image 21 is higher than or equal to the threshold, and calculates the number of living-body internal images 21 for which the probability is higher than or equal to the threshold and the number of living-body internal images 21 for which the probability is lower than the threshold.

In step A3, if the number of living-body internal images 21 for which the probability is higher than or equal to the threshold is the larger, the highlighting generation unit 44 generates highlighting information for displaying the highlighting 23 that is used when the probability is higher than or equal to the threshold. On the other hand, in step A3, if the number of living-body internal images 21 for which the probability is lower than the threshold is the larger, the highlighting generation unit 44 generates highlighting information for displaying the highlighting 23 that is used when the probability is lower than the threshold.

A case will be described in which a similarity is taken into consideration.

In step A3, the highlighting generation unit 44 calculates the similarity between a region corresponding to the target part image 22 of the target living-body internal image 21 and each of the regions corresponding to the target part images 22 of the plurality of living-body internal images 21 captured before and after the target living-body internal image 21.

Specifically, in step A3, the highlighting generation unit 44 calculates the similarity in the feature amounts f and r between different living-body internal images 21. In calculation of the similarity between living-body internal images 21, the distance between the feature vector of the feature amount f and the feature vector of the feature amount r is calculated. Alternatively, the similarity may also be expressed using a linear sum.

In step A3, the highlighting generation unit 44 then generates highlighting information in accordance with the number of probabilities that are higher than or equal to the threshold and the number of probabilities that are lower than the threshold, for each region for which the calculated similarity is higher than or equal to a threshold similarity. The similarity threshold is used to determine a different target part image, for example.

Next, the probability display generation unit 45 extracts the image capture state of a living-body internal image 21, and generates probability display information in accordance with the extracted image capture state (step A4). The image capture state is one of or a combination of two or more of the state of blur of the target part image, the state of camera shake, the state of color distribution, the state of coloration, and the state of contrast.

Specifically, in step A4, the probability display generation unit 45 obtains probability information from the calculation unit 2, corrects the obtained probability information Ci using Expression 1, and generates probability Ci'. In addition, the probability of m living-body internal images 21 captured before the target living-body internal image 21 may also be corrected based on Expression 2 and be used.

Next, the sound information generation unit 46 extracts the image capture state of a living-body internal image 21, and generates sound information in accordance with the extracted image capture state (step A5). Specifically, in step A5, the sound information generation unit 46 obtains the corrected probability from the probability display generation unit 45, and generates sound information of a sound pitch and a sound volume corresponding to the probability.

The sound information generation unit 46 uses the obtained probability to reference information in which the probability and sound information (information that includes at least one of the sound pitch, the sound volume, and the audio guidance) corresponding to the probability are associated with each other, for example, and generates sound information that is to be output to the output device 43.

Next, the output device 43 obtains, from the generation unit 3, the output information converted into a format that can be output, and outputs images shown in FIG. 3 and the like based on the output information (step A6).

In step A7, when an instruction to terminate the processing illustrated as steps A1 to A6 is obtained (step A7: Yes), the surgery assistance apparatus 1 terminates the processing. When the processing illustrated by steps A1 to A6 is to be continued (step A7: No), the surgery assistance apparatus 1 moves on to the processing in step A1.

Effects of Example Embodiment

As described above, according to the example embodiment, the surgery assistance apparatus 1 generates assistance information (one of or a combination of two or more of highlighting information, probability display information, and sound information) in accordance with one of or both a change in the region indicating a target part image and a change in the probability. Therefore, even if the image capture state of a captured target part image changes for each frame influenced by operation of the endoscope and the like, and the image capture state of the target part image undergoes an extreme change, it is possible to suppress an extreme change in assistance information. Accordingly, it is possible to prevent a human-body-part image from being difficult for the surgeon to view while preventing the assistance information from inhibiting the surgery. Therefore, the accuracy of the surgery can be improved.

[Program]

It is sufficient for a program according to the example embodiment to cause a computer to execute steps A1 to A6 shown in FIG. 11. The surgery assistance apparatus and the surgery assistance method according to the present example embodiment can be realized by installing this program in a computer and executing the installed program. In this case, the processor of the computer functions as the calculation unit 2 and the generation unit 3 (the highlighting generation unit 44, the probability display generation unit 45, and the sound information generation unit 46), and performs processing.

In addition, the program in the example embodiment may also be executed by a computer system that includes a plurality of computers. In this case, for example, each of the computers may function as one of the calculation unit 2 and the generation unit 3 (the highlighting generation unit 44, the probability display generation unit 45, and the sound information generation unit 46).

[Physical Configuration]

Figure 12:
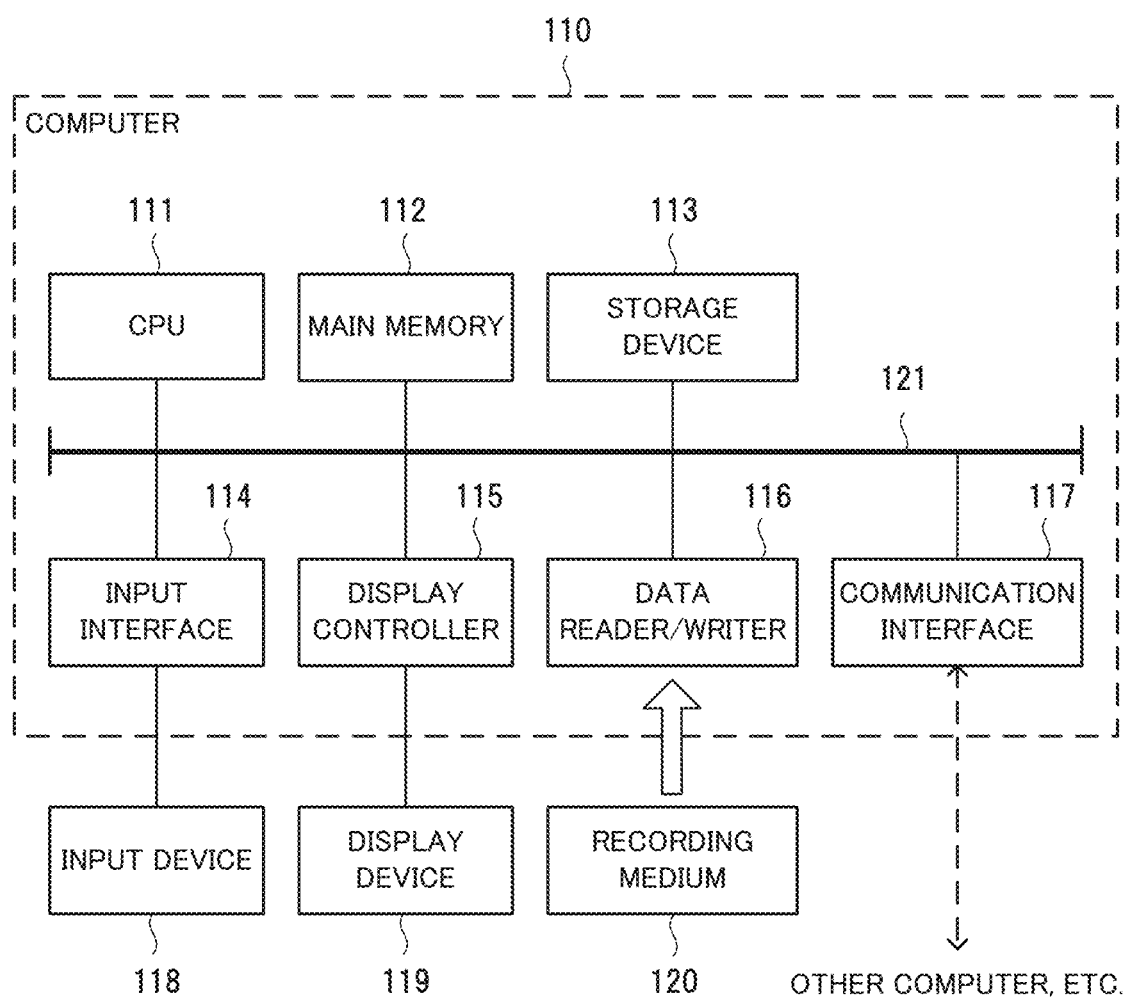
FIG. 12 is a diagram for illustrating an example of a computer that realizes the surgery assistance apparatus.

Here, a computer for realizing the surgery assistance apparatus by executing the program in the example embodiment will be described with reference to FIG. 12. FIG. 12 is a block diagram for illustrating an example of a computer that realizes the surgery assistance apparatus according to an example embodiment of the present invention.

As shown in FIG. 12, a computer 110 includes a CPU 111, a main memory 112, a storage device 113, an input interface 114, a display controller 115, a data reader/writer 116, and a communication interface 117. These constituent elements are connected to each other via a bus 121 to enable mutual data communication. Note that the computer 110 may also include a GPU (Graphics Processing Unit) or a FPGA (Field-Programmable Gate Array) in addition to or in place of the CPU 111.

The CPU 111 carries out various types of computation by deploying, in the main memory 112, programs (codes) in the example embodiment stored in the storage device 113, and executing them in a predetermined order. Typically, the main memory 112 is a volatile storage device such as a DRAM (Dynamic Random Access Memory). In addition, the program in the example embodiment is provided in a state of being stored in a computer-readable recording medium 120. Note that the program in the example embodiment may also be distributed on the Internet connected via the communication interface 117.

In addition, specific examples of the storage device 113 include a hard disk drive and a semiconductor storage device, such as a flash memory. The input interface 114 mediates data transmission between the CPU 111 and an input device 118 including a keyboard and a mouse. The display controller 115 is connected to a display device 119 to control display on the display device 119.

The data reader/writer 116 mediates data transmission between the CPU 111 and the recording medium 120, reads out a program from the recording medium 120, and writes a processing result of the computer 110 to the recording medium 120. The communication interface 117 mediates data transmission between the CPU 111 and another computer.

In addition, specific examples of the recording medium 120 include a general-purpose semiconductor storage device such as a Compact Flash (CF (registered trademark)) and a Secure Digital (SD), a magnetic recording medium such as a flexible disk, or an optical recording medium such as a compact disk read-only memory (CD-ROM).

[Supplementary Note]

In relation to the above example embodiment, the following Supplementary notes are further disclosed. Part of or all of the above-described example embodiments can be expressed in the below-described (Supplementary note 1) to (Supplementary note 18) but the present invention is not limited to the following description.

(Supplementary Note 1)

A surgery assistance apparatus including:
a calculation unit configured to calculate, based on a living-body internal image captured using an endoscope, region information indicating a region of a target part image corresponding to a target part and probability information indicating a probability of the target part image being an image of the target part; and a generation unit configured to generate assistance information for assisting surgery while suppressing an extreme change when one of or both a change in the region information and a change in the probability information are extreme.

(Supplementary Note 2)

The surgery assistance apparatus according to Supplementary Note 1, wherein the assistance information includes one or more of highlighting information that is used to highlight the region, probability display information that is used for probability display, and sound information for making a notification, with sound, that the target part has been detected.

(Supplementary Note 3)

The surgery assistance apparatus according to Supplementary Note 2, wherein the generation unit calculates, using probabilities of a plurality of living-body internal images captured before and after a target living-body internal image, the number of probabilities that are higher than or equal to a threshold and the number of probabilities that are lower than the threshold, and generates the assistance information in accordance with the calculated numbers of probabilities.

(Supplementary Note 4)

The surgery assistance apparatus according to Supplementary Note 2 or 3, wherein the generation unit calculates a similarity between the region of the target living-body internal image and each of the regions of the plurality of living-body internal images captured before and after the target living-body internal image, and generates, for each region for which a calculated similarity is higher than or equal to a similarity threshold, the assistance information in accordance with the number of probabilities that are higher than or equal to the threshold and the number of probabilities that are lower than the threshold.

(Supplementary Note 5)

The surgery assistance apparatus according to any one of Supplementary Notes 1 to 4, wherein the generation unit extracts an image capture state of the living-body internal image, and generates the assistance information in accordance with the extracted image capture state.

(Supplementary Note 6)

The surgery assistance apparatus according to Supplementary Note 5, wherein the image capture state is one of or a combination of two or more of a state of blur of the living-body internal image, a state of camera shake, a state of color distribution, a state of coloration, and a state of contrast.

(Supplementary Note 7)

A surgery assistance method comprising:

a step of calculating, based on a living-body internal image captured using an endoscope, region information indicating a region of a target part image corresponding to a target part and probability information indicating a probability of the target part image being an image of the target part; and a step of generating assistance information for assisting surgery while suppressing an extreme change when one of or both a change in the region information and a change in the probability information are extreme.

(Supplementary Note 8)

The surgery assistance method according to Supplementary Note 7, wherein the assistance information includes one or more of highlighting information that is used to highlight the region, probability display information that is used for probability display, and sound information for making a notification, with sound, that the target part has been detected.

(Supplementary Note 9)

The surgery assistance method according to Supplementary Note 8, wherein, in the step of generating, the number of probabilities that are higher than or equal to a threshold and the number of probabilities that are lower than the threshold are calculated using probabilities of a plurality of living-body internal images captured before and after a target living-body internal image, and the assistance information is generated in accordance with the calculated numbers of probabilities.

(Supplementary Note 10)

The surgery assistance method according to Supplementary Note 8 or 9, wherein, in the step of generating, a similarity between the region of the target living-body internal image and each of the regions of the plurality of living-body internal images captured before and after the target living-body internal image is calculated, and the assistance information is generated, for each region for which a calculated similarity is higher than or equal to a similarity threshold, in accordance with the number of probabilities that are higher than or equal to the threshold and the number of probabilities that are lower than the threshold.

(Supplementary Note 11)

The surgery assistance method according to any one of Supplementary Notes 8 to 10, wherein, in the step of generating, an image capture state of the living-body internal image is extracted, and the assistance information is generated in accordance with the extracted image capture state.

(Supplementary Note 12)

The surgery assistance method according to Supplementary Note 11, wherein the image capture state is one of or a combination of two or more of a state of blur of the living-body internal image, a state of camera shake, a state of color distribution, a state of coloration, and a state of contrast.

(Supplementary Note 13)

A computer-readable recording medium that includes a program recorded thereon, the program including instructions that cause a computer to carry out:

a step of calculating, based on a living-body internal image captured using an endoscope, region information indicating a region of a target part image corresponding to a target part and probability information indicating a probability of the target part image being an image of the target part; and a step of generating assistance information for assisting surgery while suppressing an extreme change when one of or both a change in the region information and a change in the probability information are extreme.

(Supplementary Note 14)

The computer-readable recording medium according to Supplementary Note 13, wherein the assistance information includes one or more of highlighting information that is used to highlight the region, probability display information that is used for probability display, and sound information for making a notification, with sound, that the target part has been detected.

(Supplementary Note 15)

The computer-readable recording medium according to Supplementary Note 14, wherein, in the step of generating, the number of probabilities that are higher than or equal to a threshold and the number of probabilities that are lower than the threshold are calculated using probabilities of a plurality of living-body internal images captured before and after a target living-body internal image, and the assistance information is generated in accordance with the calculated numbers of probabilities.

(Supplementary Note 16)

The computer-readable recording medium according to Supplementary Note 14 or 15, wherein, in the step of generating, a similarity between the region of the target living-body internal image and each of the regions of the plurality of living-body internal images captured before and after the target living-body internal image is calculated, and the assistance information is generated, for each region for which a calculated similarity is higher than or equal to a similarity threshold, in accordance with the number of probabilities that are higher than or equal to the threshold and the number of probabilities that are lower than the threshold.

(Supplementary Note 17)

The computer-readable recording medium according to any one of Supplementary Notes 14 to 16, wherein, in the step of generating, an image capture state of the living-body internal image is extracted, and the assistance information is generated in accordance with the extracted image capture state.

(Supplementary Note 18)

The computer-readable recording medium according to Supplementary Note 17, wherein the image capture state is one of or a combination of two or more of a state of blur of the living-body internal image, a state of camera shake, a state of color distribution, a state of coloration, and a state of contrast.

Although the present invention has been described above with reference to the example embodiments above, the invention is not limited to the above example embodiments. Various modifications understandable to a person skilled in the art can be made to configurations and details of the invention, within the scope of the invention.

This application is based upon and claims the benefit of priority from Japanese Patent Application No. 2019-024022, filed Feb. 13, 2019, the disclosure of which is incorporated herein in its entirety by reference.

INDUSTRIAL APPLICABILITY

As described above, according to the invention, the accuracy of surgery can be improved by presenting stable assistance information (display/sound) to a surgeon. The present invention is useful in fields in which endoscopic surgery is required.

REFERENCE SIGNS LIST

1 Surgery assistance apparatus
2 Calculation unit
3 Generation unit
21, 21a, 21b, 21c, 51 Living body internal image
22, 22a, 22b, 22c, 53 Target part image
23, 23a, 23b, 23c Highlighting information
41 Control unit
42 Endoscope
43 Output device
44 Highlighting generation unit
45 Probability display generation unit
46 Sound information generation unit
52 Image
61 Window
62 Region
81 Feature amount information
110 Computer
111 CPU
112 Main memory
113 Storage device
114 Input interface
115 Display controller
116 Data reader/writer
117 Communication interface
118 Input device
119 Display device
120 Recording medium
121 Bus

What is claimed is:

1. A surgery assistance apparatus comprising:
one or more memories storing instructions; and
one or more processors configured to execute the instructions to:
calculate, based on a living-body internal image captured using an endoscope, region information indicating a region of a target part image corresponding to a target part and probability information indicating a probability of the target part image being an image of the target part;
determine, with respect to probabilities of a plurality of living-body internal images captured before and after a target living-body internal image, a first number of the probabilities that are higher than or equal to a threshold and a second number of the probabilities that are lower than the threshold; and
generate assistance information for assisting surgery in accordance with the calculated first and second numbers of the probabilities,
wherein the assistance information includes one or more of highlighting information used to highlight the region, probability display information used for probability display, and sound information for outputting a notification, with sound, that the target part has been detected.

2. The surgery assistance apparatus according to claim 1, wherein the one or more processors are configured to execute the instructions to extract an image capture state of the living-body internal image, and generates the assistance information in accordance with the extracted image capture state.

3. The surgery assistance apparatus according to claim 2,
wherein the image capture state is one of or a combination of two or more of a state of blur of the living-body internal image, a state of camera shake, a state of color distribution, a state of coloration, and a state of contrast.

4. The surgery assistance apparatus according to claim 1,
wherein the one or more processors are configure to execute the instructions to unit calculate a similarity between a region of the target living-body internal image and a region of each of the plurality of living-body internal images, and generate, for each region for which the calculated similarity is higher than or equal to a similarity threshold, the assistance information in accordance with the first and second numbers of the probabilities.

5. A surgery assistance method performed by a computer and comprising:
   calculating, based on a living-body internal image captured using an endoscope, region information indicating a region of a target part image corresponding to a target part and probability information indicating a probability of the target part image being an image of the target part;
   determining, with respect to probabilities of a plurality of living-body internal images captured before and after a target living-body internal image, a first number of the probabilities that are higher than or equal to a threshold and a second number of the probabilities that are lower than the threshold; and
   generating assistance information for assisting surgery in accordance with the calculated first and second numbers of the probabilities,
   wherein the assistance information includes one or more of highlighting information used to highlight the region, probability display information used for probability display, and sound information for outputting a notification, with sound, that the target part has been detected.

6. The surgery assistance method according to claim 5,
wherein an image capture state of the living-body internal image is extracted, and the assistance information is generated in accordance with the extracted image capture state.

7. The surgery assistance method according to claim 6,
wherein the image capture state is one of or a combination of two or more of a state of blur of the living-body internal image, a state of camera shake, a state of color distribution, a state of coloration, and a state of contrast.

8. The surgery assistance method according to claim 5,
wherein a similarity between a region of the target living-body internal image and a region of each of the plurality of living-body internal images is calculated, and the assistance information is generated for each region for which the calculated similarity is higher than or equal to a similarity threshold in accordance with the first and second numbers of the probabilities.

9. A non-transitory computer-readable recording medium storing a program executable by a computer to perform processing comprising:
   calculating, based on a living-body internal image captured using an endoscope, region information indicating a region of a target part image corresponding to a target part and probability information indicating a probability of the target part image being an image of the target part;
   determining, with respect to probabilities of a plurality of living-body internal images captured before and after a target living-body internal image, a first number of the probabilities that are higher than or equal to a threshold and a second number of the probabilities that are lower than the threshold; and
   generating assistance information for assisting surgery in accordance with the calculated first and second numbers of the probabilities,
   wherein the assistance information includes one or more of highlighting information used to highlight the region, probability display information used for probability display, and sound information for outputting a notification, with sound, that the target part has been detected.

* * * * *